(12) United States Patent
Mead et al.

(10) Patent No.: US 8,171,585 B2
(45) Date of Patent: May 8, 2012

(54) LIGHTWEIGHT FLUID

(75) Inventors: Steven Mead, Glenwood Springs, CO (US); Richard Runkles, Longmont, CO (US)

(73) Assignee: Brock USA LLC, Boulder, CO (US)

( * ) Notice: Subject to any disclaimer, the term of this patent is extended or adjusted under 35 U.S.C. 154(b) by 871 days.

(21) Appl. No.: 12/201,751

(22) Filed: Aug. 29, 2008

(65) Prior Publication Data
US 2009/0077723 A1 Mar. 26, 2009

Related U.S. Application Data

(60) Provisional application No. 60/968,736, filed on Aug. 29, 2007.

(51) Int. Cl.
*B32B 1/04* (2006.01)
*B32B 18/00* (2006.01)
*A47C 27/08* (2006.01)

(52) U.S. Cl. .......... 5/655.4; 5/702; 2/455; 428/76; 428/325; 428/327; 24/118.1

(58) Field of Classification Search ........... 5/702, 655.4; 2/413, 455; 428/76, 325, 327; 248/118.1
See application file for complete search history.

(56) References Cited

U.S. PATENT DOCUMENTS

| | | |
|---|---|---|
| 4,252,910 A | 2/1981 | Schaefer |
| 5,079,786 A | 1/1992 | Rojas |
| 5,421,874 A | 6/1995 | Pearce |
| 5,475,882 A | 12/1995 | Sereboff |
| 5,513,899 A | 5/1996 | Michaels et al. |
| 5,549,743 A | 8/1996 | Pearce |
| 5,590,430 A | 1/1997 | Sereboff |
| 5,675,844 A | 10/1997 | Guyton et al. |
| 5,766,704 A | 6/1998 | Allen et al. |
| 5,827,459 A | 10/1998 | Allen et al. |
| 5,869,164 A | 2/1999 | Nickerson et al. |
| 5,881,409 A | 3/1999 | Pearce |
| 5,895,805 A | 4/1999 | Darling |
| 5,920,915 A | 7/1999 | Bainbridge et al. |
| 5,939,157 A | 8/1999 | Allen et al. |
| 5,955,159 A | 9/1999 | Allen et al. |
| 5,985,383 A | 11/1999 | Allen et al. |
| 6,020,055 A | 2/2000 | Pearce |

(Continued)

OTHER PUBLICATIONS

International Search Report and Written Opinion dated Mar. 20, 2009 pertaining to International application No. PCT/US2008/074812.

*Primary Examiner* — Michael Trettel
(74) *Attorney, Agent, or Firm* — Dinsmore & Shohl LLP

(57) ABSTRACT

An inexpensive, lightweight, compressible, shock absorbing, and resilient fluid for use in padding applications is presented. A fluid pad can comprise closed-cell foam beads and a surrounding fluid housed in a thin plastic bladder. The closed-cell foam beads can be exactly flooded by the fluid. Alternatively, the fluid can lubricate the closed-cell foam beads. The surrounding fluid may also comprise solid phase microballoons. The addition of the closed-cell foam beads can result in the overall fluid in the bladder being lighter in weight. The fluid pad with the closed-cell foam beads can be compressible and resilient. The fluid pad with the closed-cell foam beads can be shock absorbing with respect to impact loads or vibrations. The addition of the closed-cell foam beads can lower the cost of the fluid pad insert.

5 Claims, 4 Drawing Sheets

U.S. PATENT DOCUMENTS

| | | |
|---|---|---|
| 6,032,300 A | 3/2000 | Bainbridge et al. |
| 6,171,688 B1 * | 1/2001 | Zheng et al. ............... 428/313.5 |
| 6,197,099 B1 | 3/2001 | Pearce |
| 6,393,642 B1 * | 5/2002 | Pollman et al. ................... 5/706 |
| 6,453,477 B1 | 9/2002 | Bainbridge et al. |
| 6,455,623 B1 | 9/2002 | Howard |
| 6,583,199 B2 | 6/2003 | Brother et al. |
| 6,672,548 B1 * | 1/2004 | Yates ............................ 248/118 |
| 6,756,426 B2 | 6/2004 | Brother et al. |
| 6,835,763 B2 | 12/2004 | Ellis et al. |
| 6,986,170 B2 | 1/2006 | Nelson |
| 7,051,389 B2 | 5/2006 | Wassilefky |
| 7,168,104 B2 | 1/2007 | Tobergte |
| 7,754,791 B2 * | 7/2010 | Sereboff ......................... 524/27 |
| 2007/0105969 A1 | 5/2007 | Warnshuis et al. |
| 2007/0105970 A1 | 5/2007 | Warnshuis et al. |
| 2007/0163571 A1 * | 7/2007 | Sereboff ....................... 126/599 |

* cited by examiner

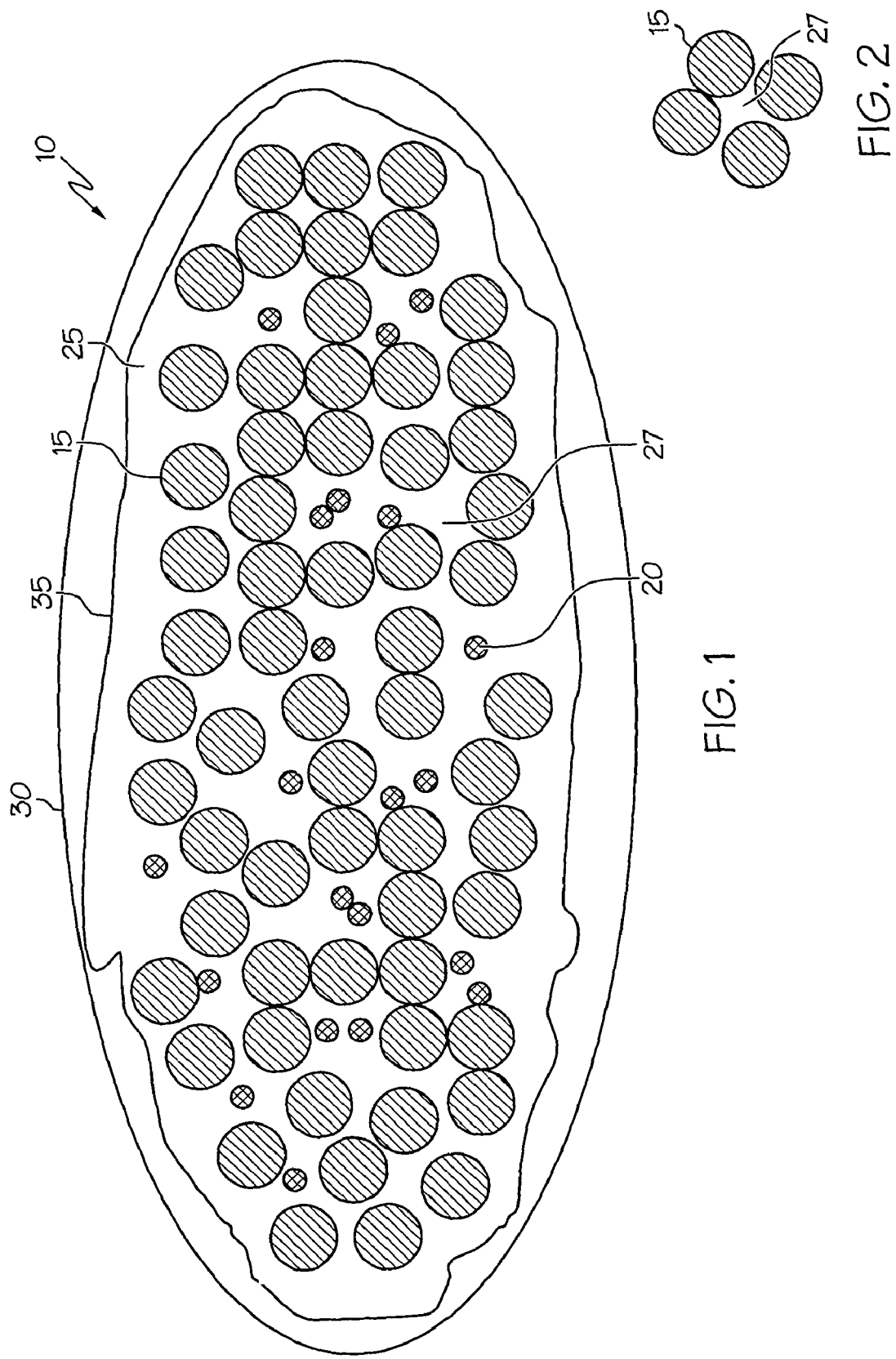

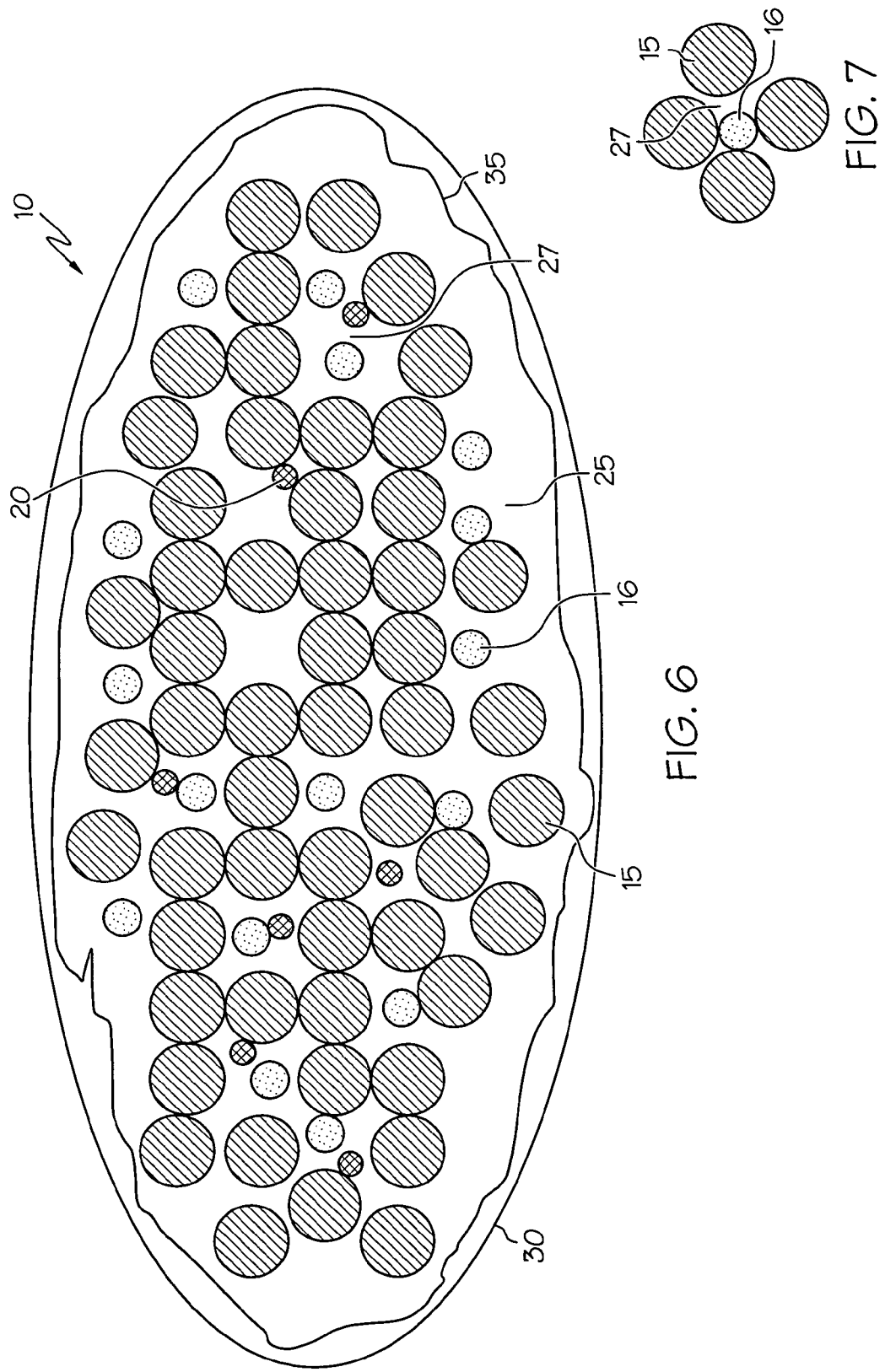

LIGHTWEIGHT FLUID

CROSS-REFERENCE TO RELATED APPLICATIONS

This application claims the benefit of U.S. Provisional Application Ser. No. 60/968,736, filed Aug. 29, 2007.

BACKGROUND

The present disclosure generally relates to padding and, in particular, relates to an inexpensive, lightweight, compressible, resilient, shock absorbing fluid for use in padding applications.

SUMMARY

Lightweight fluid can be used in medical applications to distribute pressure on the skin to avoid pressure sores. Wheelchair cushions, hospital beds and long term care beds can be some applications for lightweight fluid. Lightweight fluids can also be used in sports padding to prevent injuries. Additionally, the lightweight fluids can also be used in comfort seating and bedding products for able bodied people due to the fact that pressure on the skin in a seated or supine position results in discomfort even in able-bodied people. Lightweight fluids can also be used in other applications such as, for example, saddle pads for horses, padding for personal protection devices such as, for example, bullet-proof vests, sports padding such as, for example, hockey pads, football pads and the like, and for padding for helmets such as, for example, military helmets, bicycle helmets, or other sporting helmets, such as football and hockey helmets. Therefore, there is a need for an inexpensive, lightweight, compressible, resilient, shock absorbing fluid to be used in padding applications such as, for example comfort seating and bedding for increased comfort.

According to the present disclosure, an inexpensive, lightweight, compressible, shock absorbing and resilient composite fluid for use in padding is presented.

In accordance with one embodiment of the present disclosure, relatively large closed-cell foam beads can be added to a surrounding fluid in large quantities by volume.

Accordingly, it is a feature of the embodiments of the present disclosure to produce an inexpensive, lightweight, compressible, shock absorbing and resilient composite fluid for use in padding. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a cross-sectional view of an inexpensive, lightweight, compressible, shock absorbing and resilient fluid for use in padding according to an embodiment of the present disclosure.

FIG. 2 illustrates an expanded view of the cross-sectional view of an inexpensive, lightweight, shock absorbing, compressible and resilient fluid for use in padding shown in FIG. 1 according to an embodiment of the present disclosure.

FIG. 6 illustrates another cross-sectional view of an inexpensive, lightweight, shock absorbing, compressible and resilient fluid for use in padding according to an embodiment of the present disclosure.

FIG. 7 illustrates an expanded view of another cross-sectional view of an inexpensive, lightweight, shock absorbing, compressible and resilient fluid for use in padding shown in FIG. 6 according to an embodiment of the present disclosure.

DETAILED DESCRIPTION

Figure 3:
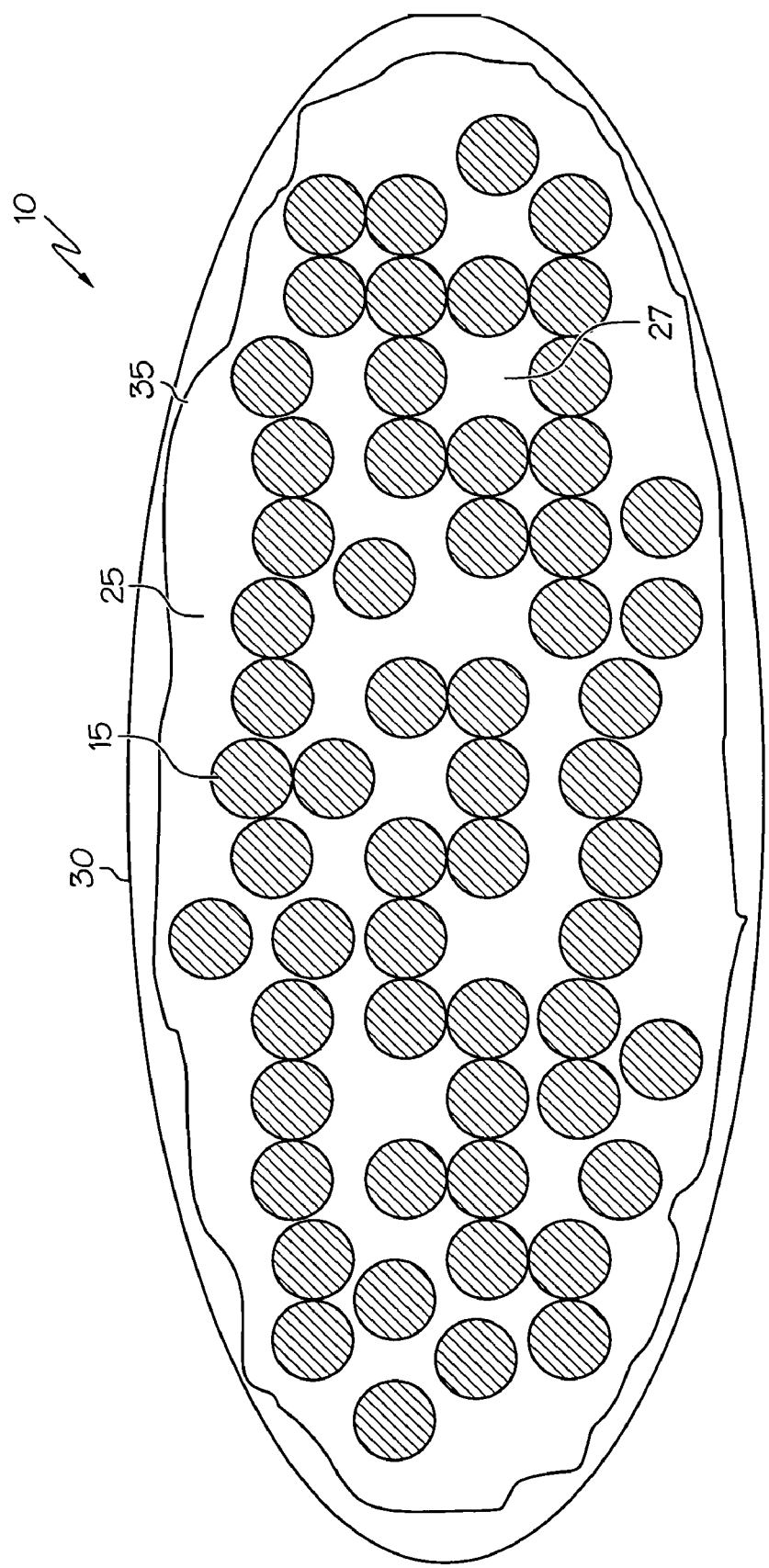
FIG. 3 illustrates another cross-sectional view of an inexpensive, lightweight, shock absorbing, compressible and resilient fluid for use in padding according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A fluid can be any substance that flows under an applied shear stress regardless of the magnitude of the applied stress. A fluid may be shape-retaining or not. Some typical shape-retaining lightweight "fluids" used in padding applications can technically be Bingham plastics, or thixotropic fluids, that can be easily pushed into a shape with very little force, but retain that shape when the force is removed. These fluids can behave like toothpaste. The shape retaining fluids do not flow due to gravity, or they flow very slowly. Lightweight fluids can be contained in bladders or containers made from plastic film. The plastic film bladders can be very soft and flexible so as to allow the fluid to conform to body contours of a user. The bladders can then be incorporated into an overall padding device design for a specific use.

Commercial lightweight shape-retaining fluid systems typically relied on one of the two following approaches: flooded microballoon systems or lubricated microballoons. In flooded microballoon systems, a fluid, most commonly a shape-retaining phase fluid (something like a grease), can be mixed with a solid phase lightweight filler material, typically phenolic, glass, or plastic hollow microballoons with diameters from 0 to 300 microns. Flooded microballoon fluids can generally be incompressible unless they contain deformable (typically plastic) microballoons. When flooded microballoon fluids contain deformable microballoons, the fluids can be compressible.

However, the flooded microballoon fluids with deformable microballoons can require quite a bit of pressure to effect any appreciable change in volume. When these lightweight fluids can be subjected to about 30 to 40 psi such as, for example, when they are pumped from one container to another, the lightweight fluids will compress appreciably but the fluids can require a very long time (e.g., more than a day) to recover their original volume after the pressure is removed. Therefore, these fluids are not very resilient. In contrast, a resilient fluid returns to its original form relatively quickly after a compression force is removed. In most applications, the actual pressure on a fluid pad can be much less than required for commercial lightweight fluids to compress to a lower volume. Therefore, the commercial lightweight fluids can be considered to be non-compressible and non-resilient in most actual use applications for most practical purposes.

In the flooded microballoon system approach, the fluid volume can fill up the interstitial spaces between the microballoons so the system is "flooded" with respect to the microballoons and there can be no air spaces in the bladder interior. However, the flooded microballoon systems typically can have more fluid than may be needed to fill up the interstitial spaces between the microballoons, so the microballoons can be free-floating in the fluid. Common specific gravities for these fluids can range from about 0.4 to about 0.8.

Several problems can be associated with these fluids in a flooded system. For example, it can be difficult to keep the lightweight microballoons from floating out of the fluid, especially with temperature changes and variable pressures from use. When the microballoons do float out of the fluid, they may create a "hard spot" against the bladder wall. These hard spots can be potential sources of high pressure on the skin that may result in discomfort or result in skin breakdown. It can also difficult to maintain a reasonably constant viscosity with changing temperature, otherwise the body heat of the person using the cushion will heat up the fluid over time, resulting in less postural stability than when the fluid is at room temp.

In the case of a lubricated microballoons system, the lubricating fluid can be used only to coat the microballoons. The system cannot be flooded with respect to the microballoons, and there can be air spaces between the microballoons. However, the system as a whole still can act as a shape-retaining fluid. Common specific gravities of these fluids can range from about 0.2 to about 0.4.

Several problems can be associated with these shape-retaining lubricated microballoon fluids. For example, the shape-retaining fluids do not flow very easily and generally can have a stiffer "feel." This can reduce the ability of the cushion to conform to the body and can increase pressure on the skin potentially resulting in discomfort or potentially resulting in skin breakdown. It can also be difficult to maintain a reasonably constant viscosity with changing temperature, otherwise the body heat of the person using the cushion will heat up the fluid over time, resulting in less postural stability than when the shape-retaining fluid is at room temp.

Typically, both the flooded microballoon system and the lubricated microballoons systems can have additional requirements placed on them. Both systems can be required by many regulatory agencies to be fire resistant. The fluids can also need to have biocompatibility with skin. They should be non-toxic in case a child or non-cognizant adults breaks open the housing bladder and eats the fluid. The fluids can need to be non-staining if the bladder bursts and fluids get on clothes or furniture. Further, they can need to be odor free. For the fluids to have a long product life, the fluids should maintain a chemical stability over many years of use. Finally, the fluids should also have a chemical compatibility with the bladder material so that the bladder material does not weaken over time which might cause rupture of the bladder.

The presented disclosure can be an improvement to both types of lightweight, shape-retaining fluid systems discussed above (i.e., flooded microballoon systems and lubricated microballoons). The improvement can be to add relatively large closed-cell foam beads to the surrounding fluid in large quantities by fluid volume to make a composite fluid. The large closed-cell foam beads can be significantly larger and, therefore, take up more volume than the surrounding fluid. Further, the typical specific gravity of the closed-cell foam beads can be much less than the specific gravity of the surrounding fluid, thereby, reducing the overall fluid weight significantly. In addition, the composite fluid with the addition of the closed-cell foam beads can be more compressible because the closed-cell foam beads can deform under low pressure resulting in the overall composite fluid being compressible under low pressures. The composite fluid with the addition of the closed-cell foam beads can be more resilient by relatively quickly recovering in volume after a deforming load is removed. In addition, the composite fluid with the addition of the closed-cell foam beads can be more shock absorbing, both to large shock loads and to vibration. Additionally, the closed-cell foam beads generally can be less expensive than the surrounding fluid itself, thereby, by adding the closed-cell foam beads to the composite fluid, the overall cost of the fluid can be reduced considerably.

Referring to FIG. 1, a cross-sectional view of an inexpensive, lightweight, shock absorbing, compressible, and resilient composite fluid 35 for use in fluid pad 10 is illustrated. The fluid pad 10 can comprise a housing bladder 30 that can be filled with a surrounding fluid 25 that can comprise a shape-retaining fluid such as, for example, a Bingham plastic or a thixotropic fluid, and microballoons 20. Closed-cell foam beads 15 can be added to the surrounding fluid 25 in sufficient quantities so that the system can be exactly flooded with respect to the large closed-cell foam beads 15. It should be noted that the surrounding fluid 25 surrounding the closed-cell foam beads 15 may contain microballoons 20 or it may not. The surrounding fluid 25 may be shape retaining or it may not. In any case, the surrounding fluid 25 can act like a fluid with respect to the large closed-cell foam beads 15. The microballoons 20 can be microscopic and can be considerable smaller than the large closed-cell foam beads 15. By exactly flooded, the surrounding fluid 25 can substantially only occupy the interstitial spaces 27 between the closed-cell foam beads 15 and the closed-cell foam beads 15 do not float out of contact with their neighboring closed-cell foam beads 15. FIG. 2 illustrates the interstitial spacing 27 between the closed-cell foam beads 15. Since the structure of the closed-cell foam beads 15 can be closed-cell, the surrounding fluid 25 does not migrate into the interior of the closed-cell foam beads 15.

In an exactly flooded composite system, the surrounding fluid 25 can occupy between about 15% to about 35% of the overall volume of the fluid pad 10. The volume of the surrounding fluid 25 in the fluid pad 10 can make the system exactly flooded (with respect to the large closed-cell foam beads 15, not the small microballoons 20) with no air in the interstitial spaces 27. In other words, the closed-cell foam beads 15 do not float out of the system and become lodged against the wall of the housing bladder 30 because there cannot enough surrounding fluid 25 to allow the closed-cell foam beads 15 to float.

Figure 5:
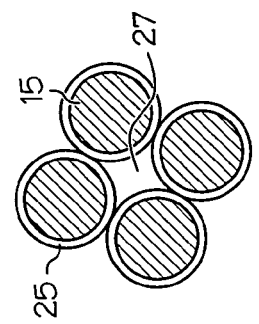
FIG. 5 illustrates an expanded view of another cross-sectional view of an inexpensive, lightweight, shock absorbing, compressible and resilient fluid for use in padding according to an embodiment of the present disclosure.

Alternatively, in another embodiment, the closed-cell foam beads 15 can be added to the surrounding fluid 25 in the housing bladder 30 in greater quantity than the exactly flooded system, so that there can be air in the interstitial spaces 27 between the closed-cell foam beads 15 and surrounding fluid 25 coats the closed-cell foam beads 15 as shown in FIG. 5. In this embodiment, the surrounding fluid 25 can essentially act as a lubricant around the closed-cell foam beads 15. However, this fluid pad 10 can have the potential problem of requiring more pressure to move the surrounding fluid 25, potentially increasing pressure on the skin of the user. In this embodiment, the composite system can be said to be underflooded with respect to the large closed-cell foam beads 15.

Figure 4:
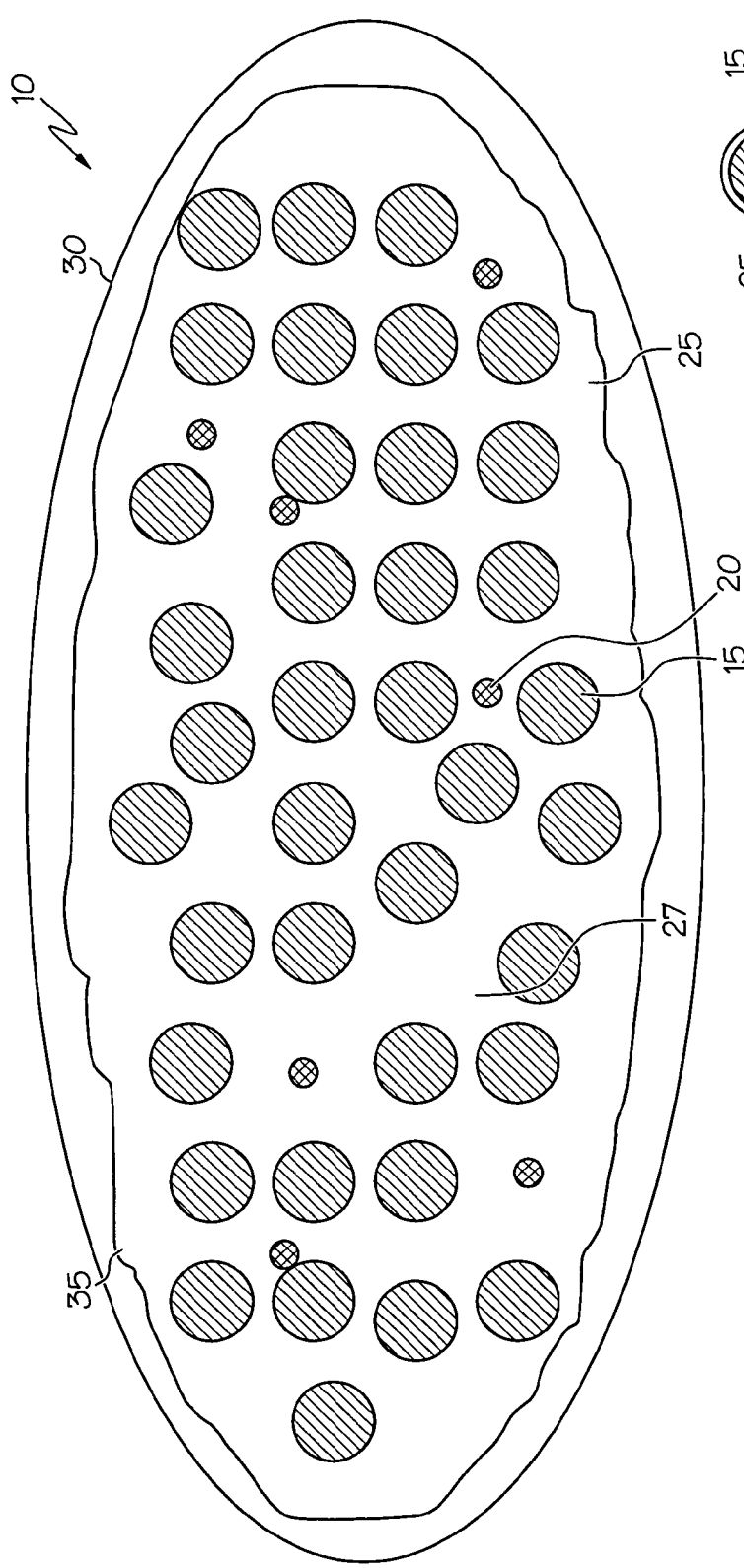
FIG. 4 illustrates another cross-sectional view of an inexpensive, lightweight, shock absorbing, compressible and resilient fluid for use in padding according to an embodiment of the present disclosure.

In yet another embodiment, the closed-cell foam beads 15 can be added to the surrounding fluid 25 in housing bladder 30 in lesser quantities than the exactly flooded system, so that the closed-cell foam beads 15 and the microballoons 20 can be essentially floating in the surrounding fluid 25, as shown in FIG. 4. In this embodiment, the composite system can be exceedingly flooded.

In still another exemplary embodiment, the large closed-cell foam beads 15 can be used with a non-shape-retaining surrounding fluids 25 (i.e., not a fluid such as, for example, lightweight Bingham plastics or thixotropic fluids which use microballoon 20 fillers). Non-shape-retaining surrounding fluids 25 can be for example, oil, water, silicone oil or greases or any other common fluid. The volume of the non-shape-retaining surrounding fluids 25 can be exactly flooded, exceedingly flooded, or underflooded with respect to the large closed-cell foam beads 15 as described above for the shape-retaining surrounding fluids 25.

The housing bladder 30 of the fluid pad 10 can be a flexible plastic film envelope. In cases where the composite fluid 35 is generally non-shape retaining such as, for example, an exceedingly flooded system comprising a non-shape retaining surrounding fluid 25 such as, for example, a low viscosity silicone oil, the plastic film can add enough structure to the overall composite pad so that pad can be able to able to retain its shape after an applied force to the pad is removed. In other words, the overall non-shape-retaining composite fluid 35 mixture of the non-shape retaining surrounding fluid 25 and closed-cell foam beads 15 in a housing bladder 30 (as shown in FIG. 3) can act very much like housing bladders 30 filled with shape-retaining lightweight fluids such as, for example, lightweight Bingham plastics or thixotropic fluids, without the addition of microballoons 20. The housing bladders 30 can generally maintain their shape when pressure is removed from the fluid pad 10, making the fluid pad 10 as a whole shape-retaining.

In still yet another embodiment, the different sized closed-cell foam beads 15, 16 can be added to the surrounding fluid 25 in housing bladder 30 as illustrated in FIG. 6. The smaller closed-cell foam beads 16 can fill some of the interstitial spaces 27 that may exist between the larger closed-cell foam beads 15 as shown in FIG. 7. The surrounding fluid 25 may contain microballoons 20. This embodiment also can result in a lighter composite fluid 35 due to the fact that more of the volume within the housing bladder 30 can be comprised of the very low density closed-cell foam beads 15, 16. In practice, a given batch of closed-cell foam beads 15 can have a statistical distribution of sizes of foam beads 15 as well as a variety of different shapes of foam beads 15.

Concerning the closed-cell foam beads 15, in some applications it can be desirable to have the closed-cell foam beads 15 as soft as possible in order to be compressible under low pressures created low pressure application such as, for example, people sitting on fluid pads 10 or lying on fluid-filled mattresses, thereby further conforming to the skin of the user in use. For example, the fluid pads 10 subjected to static loads of a person sitting on a seat cushion can be under internal fluid static pressure of 5 psi or less. At 5 psi, the microballoons 20 (if the system comprises microballoons 20) do not exhibit enough change in volume to have an appreciable effect. The internal fluid static pressure of a fluid pad 10 can be determined by filling a housing bladder 30 with water and measuring the static pressure of the water in the housing bladder 30 using a manometer, as is known in the art. In some seating applications, the fluid static pressure has been measured to be 2 psi or less.

The addition of the closed-cell foam beads 15 to the fluid also can allow the fluid pads 10 to recover their original volume relatively quickly (e.g., a few hours) after the pressure is removed. In other words, the addition of the closed-cell foam beads 15 can increase the resiliency of the surrounding fluid 25. Harder closed-cell foam beads 15 tend to move within the surrounding fluid 25 in response to pressure, as opposed to softer foams beads which tend to compress in response to pressure. However, it can be foreseeable that in some applications, it may be desirable to have hard closed-cell foam beads 15 added to the surrounding fluid 25.

As mentioned above, the foam beads 15 can be closed-celled so that the foam beads 15 can substantially be impervious to the surrounding fluid 25 of the composite fluid 35 and so that the surrounding fluid 25 of the composite fluids 35 cannot penetrate the interior of the foam beads 15. It was found that soft closed-cell expanded polyethylene and expanded polypropylene can work well. Polypropylene and polyethylene beads of this type can be available commercially from JSPI, Kaneka, BASF or from any number of other suppliers. The closed-cell foam beads 15 can be about 0.07 inches to 0.5 inches and can be a variety of shapes such as, for example, round, irregular, tablet-shaped or any other suitable shape.

Additionally, the fluid pad 10 can have an increased ability to absorb shock, or impact, loads applied to the fluid pad 10. The ability of the fluid pad 10 to absorb impacts is due to the volume of the closed-cell foam beads 15 and the shock absorbing properties of the closed-cell foam beads 15. Some examples of the shock absorbing properties of the closed-cell foam beads 15 are disclosed in U.S. Pat. Nos. 5,920,915; 6,032,300; 6,055,676; 6,301,722; 6,357,054; and 6,453,477, all of which are herein incorporated by reference in their entirety. In one embodiment, the fluid pad 10 can be incorporated into helmets, sports padding and bullet proof vests, for example, to provide both comfort and shock absorption.

Example 1

JSPI 4513 expanded polyethylene beads were added to commercial silicone grease in sufficient quantity to yield an exactly flooded system. The resulting density was measured to be 0.329 g/cc. The material in a bladder such as, for example, a zip lock plastic bag, behaved very similar to a fluid pad commonly used in wheelchair cushions.

Example 2

JSPI 4513 expanded polyethylene beads were added to commercial lithium automotive grease in sufficient quantity to yield an exactly flooded system. The resulting density was measured to be 0.317 g/cc. The material in a bladder such as, for example, a zip lock plastic bag, behaved very similar to a fluid pad commonly used in wheelchair cushions.

Example 3

JSPI 4513 expanded polyethylene beads were added to Sunrise Medical wheelchair cushion fluid in sufficient quantity to yield an exactly flooded system. The resulting density was measured to be 0.190 g/cc. The material in a bladder such as, for example, a zip lock plastic bag, behaved similar to a fluid pad commonly used in wheelchair cushions.

The addition of the closed-cell foam beads 15 can result in the overall composite fluid 35 in the housing bladder 30 being lighter in weight due to the fact the closed-cell foam beads 15 typically weigh less than the surrounding fluid 25. Additionally, the fluid pad 10 with the addition of the closed-cell foam beads 15 can be compressible as well as resilient because the closed-cell foam beads 15 can deform under low pressure resulting in the overall composite fluid 35 in the housing bladder 30 being compressible under low pressures and being able to recover to substantially the original volume when the pressure is removed. In addition, the fluid pad 10 with the addition of the closed-cell foam beads 15 can be shock absorbing with respect to impact loads or vibrations because of the impact absorbing properties of the closed-cell foam beads 15. Finally, the addition of the closed-cell foam beads 15 can lower the cost of the fluid pads 10 since the closed-cell foam beads 15 can typically be less expensive than the surrounding fluid 25.

It is noted that terms like "preferably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

What is claimed is:

1. A fluid pad comprising a bladder, closed-cell foam beads and a surrounding fluid, wherein:
   the closed-cell foam beads and the surrounding fluid comprise a composite fluid;
   the closed-cell foam beads are substantially impervious to the composite fluid;
   the closed-cell foam beads are underflooded by the surrounding fluid leaving interstitial air spaces between the closed-cell foam beads; and
   the bladder houses the composite fluid within the interior of the bladder.

2. The fluid pad of claim 1, wherein the surrounding fluid comprises oil, silicon oil, grease, or combinations thereof.

3. A fluid pad comprising a bladder, closed-cell foam beads and a surrounding fluid, wherein:
   the closed-cell foam beads and the surrounding fluid comprise a composite fluid;
   the closed-cell foam beads are substantially impervious to the surrounding fluid;
   the closed-cell foam beads are exceedingly flooded by the surrounding fluid so that interstitial spaces between the closed-cell foam beads are filled with the surrounding fluid; and
   the bladder houses the composite fluid within the interior of the bladder.

4. A fluid pad comprising a bladder, small closed-cell foam beads, large closed-cell foam beads and a surrounding fluid, wherein:
   the small closed-cell foam beads, the large closed-cell foam beads and the surrounding fluid comprise a composite fluid;
   the large and small closed-cell foam beads are substantially impervious to the surrounding fluid;
   the surrounding fluid lubricates the large closed-cell foam beads leaving interstitial air spaces between the large closed-cell foam beads;
   the small closed-cell foam beads fill the interstitial air spaces between the large closed-cell foam beads; and
   the bladder houses the composite fluid within the interior of the bladder.

5. A fluid pad comprising a bladder, closed-cell foam beads and a surrounding fluid, wherein:
   the closed-cell foam beads and the surrounding fluid comprise a composite fluid;
   the closed-cell foam beads are substantially impervious to the surrounding fluid;
   the closed-cell beads comprise both soft closed-cell foam beads and hard closed-cell beads; and
   the bladder houses the composite fluid within the interior of the bladder.

* * * * *

UNITED STATES PATENT AND TRADEMARK OFFICE
CERTIFICATE OF CORRECTION

| | |
|---|---|
| PATENT NO. | : 8,171,585 B2 |
| APPLICATION NO. | : 12/201751 |
| DATED | : May 8, 2012 |
| INVENTOR(S) | : Mead et al. |

It is certified that error appears in the above-identified patent and that said Letters Patent is hereby corrected as shown below:

Col. 8, Claim 5, line 43 "the closed-cell beads" should read --the closed-cell foam beads; and Col. 8, Claim 5, line 44 "hard closed-cell beads" should read --hard closed-cell foam beads--.

Signed and Sealed this
Thirty-first Day of July, 2012

David J. Kappos
*Director of the United States Patent and Trademark Office*